United States Patent
Vossmeyer et al.

(10) Patent No.: US 7,223,367 B1
(45) Date of Patent: May 29, 2007

(54) CHEMICAL SENSOR ARRANGEMENT

(75) Inventors: Tobias Vossmeyer, Fellbach (DE); Hidemi Tomita, Stuttgart (DE)

(73) Assignee: Sony International (Europe) GmbH, Cologne (DE)

( * ) Notice: Subject to any disclaimer, the term of this patent is extended or adjusted under 35 U.S.C. 154(b) by 0 days.

(21) Appl. No.: 09/533,688

(22) Filed: Mar. 23, 2000

(30) Foreign Application Priority Data

Mar. 26, 1999 (EP) .................................. 99106337

(51) Int. Cl.
B32B 27/04 (2006.01)

(52) U.S. Cl. .............................. 422/82.05; 422/82.08; 422/82.09; 422/98; 422/88

(58) Field of Classification Search ............. 422/82.05, 422/82.08, 88, 98, 82.09, 82.07
See application file for complete search history.

(56) References Cited

U.S. PATENT DOCUMENTS

| | | | |
|---|---|---|---|
| 3,649,200 A | 3/1972 | Moore | |
| 3,718,511 A * | 2/1973 | Moulin ........................ | 117/56 |
| 4,138,336 A | 2/1979 | Mendel et al. | |
| 5,372,721 A | 12/1994 | Langhorst et al. | |
| 5,496,997 A | 3/1996 | Pope | |
| 5,503,723 A | 4/1996 | Ruddy et al. | |
| 5,640,470 A | 6/1997 | Iyer et al. | |
| 5,696,314 A * | 12/1997 | McCaffrey et al. | |
| 5,958,340 A * | 9/1999 | Meyer et al. | |
| 5,989,947 A * | 11/1999 | Dilger et al. ............... | 438/172 |
| 6,017,696 A * | 1/2000 | Heller | |
| 6,149,868 A * | 11/2000 | Natan et al. | |
| 6,197,594 B1 * | 3/2001 | Weindel et al. | |
| 6,207,369 B1 * | 3/2001 | Wohlstadter et al. | |
| 6,214,560 B1 * | 4/2001 | Yguerabide et al. | |
| 6,242,264 B1 * | 6/2001 | Natan et al. | |
| 6,263,723 B1 * | 7/2001 | Takao et al. | |
| 6,271,040 B1 * | 8/2001 | Buechler | |
| 6,297,061 B1 * | 10/2001 | Wu et al. | |
| 6,306,610 B1 * | 10/2001 | Bawendi et al. ............. | 435/7.1 |
| 6,326,144 B1 * | 12/2001 | Bawendi et al. | |
| 6,331,273 B1 * | 12/2001 | Nova et al. | |
| 6,426,127 B1 * | 7/2002 | Ross et al. ................... | 427/503 |
| 6,476,312 B1 * | 11/2002 | Barnham ..................... | 136/247 |
| 6,488,770 B1 * | 12/2002 | Meissner et al. ............. | 117/73 |
| 6,630,307 B2 * | 10/2003 | Bruchez et al. ............... | 435/6 |
| 2001/0007718 A1 * | 7/2001 | Tamura et al. ............... | 428/620 |
| 2001/0055764 A1 * | 12/2001 | Empedocles et al. .......... | 435/6 |
| 2003/0003492 A1 * | 1/2003 | Miller et al. ................... | 435/6 |

(Continued)

FOREIGN PATENT DOCUMENTS

EP    0 263 692    4/1988

(Continued)

*Primary Examiner*—Brian R. Gordon
(74) *Attorney, Agent, or Firm*—Oblon, Spivak, McClelland, Maier & Neustadt, P.C.

(57) ABSTRACT

The present invention relates to a chemical sensor arrangement having an analyte sensitive indicator wherein the analyte sensitive indicator has at least one nanoparticle. The invention further relates to a method for providing nanoparticles of defined and different sizes, especially for a chemical sensor arrangement, wherein a nanoparticle solution, having nanoparticles of a broad size distribution, is applied to chromatography beads, whereby the nanoparticles are adsorbed onto said beads and classified by size, and beads of a specific layer, having nanoparticles of essentially the same size, are separated from the beads within other layers and are held in suspension.

23 Claims, 2 Drawing Sheets

U.S. PATENT DOCUMENTS

Figure 1:
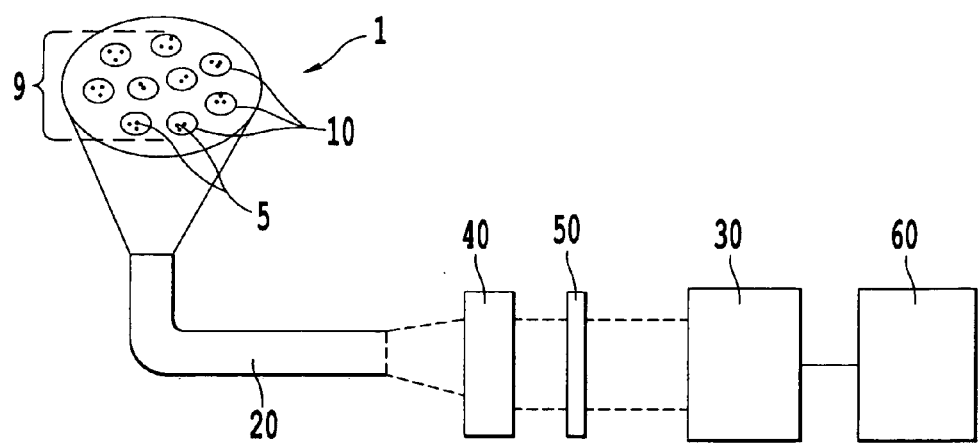

| | | |
|---|---|---|
| 2003/0127660 A1* | 7/2003 | Bawendi et al. ............... 257/89 |
| 2003/0136946 A1* | 7/2003 | Kumacheva ................. 252/500 |
| 2003/0202770 A1* | 10/2003 | Garito et al. ............... 385/141 |
| 2004/0004982 A1* | 1/2004 | Eisler et al. ................... 372/43 |
| 2004/0150268 A1* | 8/2004 | Garito et al. ................. 310/12 |
| 2005/0079551 A1* | 4/2005 | Mizuno et al. .............. 435/7.1 |
| 2005/0130258 A1* | 6/2005 | Trent et al. ................ 435/68.1 |

FOREIGN PATENT DOCUMENTS

| | | |
|---|---|---|
| WO | WO 96 07487 | 3/1996 |
| WO | WO 96 41173 | 12/1996 |
| WO | WO 98 04740 | 2/1998 |
| WO | WO 98 40726 | 9/1998 |

* cited by examiner

CHEMICAL SENSOR ARRANGEMENT

FIELD OF THE INVENTION

The present invention relates to a chemical sensor arrangement comprising an analyte sensitive indicator and further relates to a method for providing nanoparticles of defined and different sizes, especially for a chemical sensor arrangement according to this invention.

BACKGROUND OF THE INVENTION

Chemical sensors for both gases and liquid phase gain an increasing importance for the control of chemical processes and environmental issues, for medical purposes and the like. There is a wide variety of chemical sensors available on the market. The chemical sensor devices can be roughly separated as working on the basis of one of two major principles: the first is that electrochemical characteristics are affected by the adsorption of the analyte onto or into a sensitive layer or by combustion of the analyte. According to the second principle, changes in the optical properties are induced by the presence of an analyte. Both changes can be measured by respective detectors.

With respect to sensors working according to the second principle, where also the inventive sensor can be assigned to, sensor arrays are known, where the fluorescence and the optical absorption properties of organic dyes are used for chemical sensing. Such a sensor is for example disclosed in a paper of John J. Lavigne et al. "Solution-Based Analysis of Multiple Analytes by a Aensor Array: Toward the Development of an Electronic Tongue", in Journal of American Chemical Society 1998, 120, 6429–6430. The described sensor allows for the simultaneous identification of multiple analytes in solution. Poly-(ethylene glycol)-poly styrene (PEG-PS) resin beads are positioned in a 3×3 array of wells formed in a Si/SiN-wafer. Signal transduction is accomplished by analysis of the absorption properties of the beads using a CCD-camera, interfaced with the sensor array. The use of CCD-cameras and optical fibers in sensor arrangements is also explained in a paper of P. Pantano and David R. Walt "Analytical Applications of Optical Imaging Fibers" in Analytical Chemistry 1995, 481 A ff.

But, the properties of the chemical sensors according to the state of art using organic dyes have numerous disadvantages: The number of selective indicator dyes for the reversible detection of analyte molecules or ions is limited. Therefore, a broadband application in sensor arrangement is not easily achievable. Further, the organic dyes do not show a stability desired for most chemical sensor arrangements.

It is further known that fluorescence properties of a semiconductor bulk material can be changed and influenced by adsorbing chemicals at a surface. But, the utilisation of semiconductor bulk material as a chemical sensor only shows an insufficient change of optical properties upon exposure to an analyte to be detected.

OBJECTS AND SUMMARY OF THE INVENTION

It is therefore an object of the present invention to provide a chemical sensor arrangement showing a clearly detectable change of the optical properties of an array of indicators with a very short response time, high sensitivity and a long term stability.

This object is achieved by a chemical sensor arrangement wherein the analyte sensitive indicator comprises at least one nanoparticle.

The sensor arrangement preferably also comprises means for detecting optical properties of the indicator and changes thereof. It can also comprise means for detecting a current flow passing through the indicator, as the current flow may be affected by analyte absorption in case of electroluminescence.

Preferably multiple nanoparticles forming a nanoparticle assembly and/or an array of nanoparticle assemblies, is provided. The nanoparticles within one single assembly are normally of identical material, wherein preferably assemblies of different nanoparticle materials are provided. It should be noticed that it might be also possible that an array of only single nanoparticles can be provided

DETAILED DESCRIPTION OF THE INVENTION

Because of the huge surface-to-volume ratio of nanoparticles and the high porosity of nanoparticle assemblies, a large number of analyte molecules can be adsorbed by a nanoparticle and within a nanoparticle structure in a very short time. This leads to both a high sensitivity of the inventive chemical sensor comprising these nanoparticles as analyte-sensitive indicators as well as to a short response time. The sensor arrangement can well be applied in both the liquid and the gas phase.

Multiple nanoparticles will increase the adsorption ability of the sensor arrangement. An array of different nanoparticle assemblies will enable a detection of a wide range of analytes by the same sensor arrangement. This is because every nanoparticle assembly of the array comprises different nanoparticles with different chemical selectivities/sensitivities. On the other hand, it should be noticed that in some cases it may not be necessary to use a full array of different nanoparticle assemblies, but instead to use one assembly of identical nanoparticles or even one single nanoparticle alone. Using only one particle assembly or one particle alone is especially useful when the sensor is only accessible to one specific analyte, or in cases in which the concentration of only one analyte is to be measured or in which the analyte to be measured is not present in a mixture with other compounds that can interfere with the measurement. It is also useful when very small sensor arrangements are required.

Especially when single nanoparticles are utilized, a microscope with sufficient spatial resolution, e.g. a scanning nearfield optical microscope, a confocal micrsocope or a scanning tunneling microscope, is used for detection and/or excitation. Such an arrangement can be used to prepare sensor arrangements with nanoscale spatial resolution, which can be used for ultra high resolution chemical mapping.

As mentioned above, the nanoparticles of each assembly within the array preferably show different selectivities/sensitivities, in order to receive a clear identification for multiple analytes with the same sensor.

For the identification of analytes within a mixture, the signal pattern obtained from the sensor array has to be analyzed (pattern recognition analysis).

It is possible to widely provide nanoparticle indicators with different sensitivities and optical properties by choosing different nanoparticle materials or by varying the particle compositions. Further possibilities for varying the properties and sensitivities of the nanoparticle indicators can be achieved by chemical surface modifications or by varying the particle size of the nanoparticles. Therefore, a wide variety of nanoparticle indicators for selectively sensing different kinds of analytes can be achieved.

In one embodiment, the nanoparticles are metal and/or semiconductor nanoparticles.

The sensitivity and/or the optical properties can be varied by selecting semiconductors having different band gaps or by combinations of semiconductor materials.

Metal nanoparticles will preferably used for absorption measurments. As metals, preferably Ag, Au, Pt and/or Pd are used.

As semiconductor materials, preferably II/VI semiconductors, as CdS, CdSe, CdTe, ZnO, ZnS, ZnSe, ZnTe, HgS, HgSe, HgTe, or III/V semiconductors, preferably GaAs, InP, are selected. It is also possible to use a combination of two or more different materials, preferably CdSe/ZnS, CdSe/CdS, CdS/Cd(OH)$_2$ or HgS/CdS core shell structures. Other materials such as $Cd_3P_2$ may be used.

Furthermore the at least one nanoparticle may be doped with Lanthanides and/or transition metals, in order to improve the optical and possibly the chemical properties.

With the above selection of materials, the properties of the nanoparticles can be finely tuned to adapt the sensor to the desired application and/or the expected analytes to be detected.

The optical properties of nanoparticle assemblies may also be tuned by utilizing mixtures of metal and semiconductor nanoparticles within the sensor arrangement.

The size of the nanoparticles is preferably less than 1 μm, most preferred between 100 nm and 1 nm. As explained above, the sensitivities and the optical properties of the material can be tuned not only by varying the particle composition, but also by varying the particle size, leading to a shift in the energy levels, or to a shift of the band gap in case of semiconductor material, in the nanoparticle indicators.

In a preferred embodiment, the array of indicators comprises a combination of nanoparticle assemblies as indicators. In each assembly the nanoparticles are made of different materials or have different sizes or different surfaces, thereby utilizing a wide variety of tuning possibilities for fitting the chemical sensor arrangement to the desired application and to the expected analytes to be detected.

In a further embodiment, the nanoparticle assemblies have s sponge like structure. Thereby, the analyte is enabled to access the nanoparticle arrangement and the indicators in a better and faster way. The responsiveness of the sensor arrangement is thereby increased.

Such a nanostructure can e.g. be provided by using a template-supported organization of the nanoparticles, wherein the templates are removed afterwards.

Preferably, nanoparticle materials are provided, changing its photoluminescence or electroluminescence upon exposure to analytes. The change of photoluminescence or electroluminescence can be either an increasing or decreasing of intensity or a shift of wavelength or a combination of these.

Instead of luminescence properties, also the absorption characteristics of nanoparticles can change upon absorption of analyte molecules.

Luminescence normally changes in an amount that can easily be measured and detected, when the respective nanoparticles are exposed to analytes. Luminescence of nanoparticles can be induced by irradiation with a light source, preferably a UV light source, especially UV/vis light, or by electrochemical charge carrier injection and recombination of the charge carriers within the particles.

The source used to stimulate the luminescence can be applied in a constant mode or in a pulsed mode. The pulsed mode is preferred in order to prevent ageing of the indicators.

When utilzing electroluminescence for signal transduction, the nanoparticle array of the sensor has to be contacted by electrodes and a voltage has to be applied to inject charge-carriers into the nanoparticles that recombine under emission of electroluminescence. Contacting has to be carried out in a geometry allowing the analyte to get into contact with the particles.

Also the injection of charge-carriers can be conducted in a constant mode or a pulsed mode.

It is to be understood that all optical characteristics of the nanoparticle are not limited to any specific radiation spectrum, but preferably UV, UV/vis and IR regions are utilized for signal transduction.

It is noted that in the case of electroluminescence also the current passing through the sample may be affected by analyte absorption. Thus, also the changes of current may be used for signal transduction.

Preferably, the array of nanoparticle indicators are provided on at least one optical fibre. Any radiation or change of radiation, especially the change of photoluminescence, can thereby directly be transferred to a detecting means for further processing. No further carrier or substrate for the nanoparticle indicators is necessary.

Furthermore, due to the flexibility of the material, the sensor can easily be positioned also at locations normally difficult to reach, e.g. at small cavities or the like.

Preferably, the nanoparticle indicators are provided in micro-troughs that are formed on any substrate, preferably formed at the end of at least one optical fibre. Thereby an exact position of the single indicators, the particle assemblies, in the array is defined, ensuring a proper and exact detection and analysis, also of different analytes within a mixture.

Furthermore, the nanoparticles are in a more protected position within the optical fibre. External influences or damage to the nanoparticles are efficiently avoided.

The chemical sensor arrangement preferably further comprises a CCD-camera for detecting a change of the optical properties of the nanoparticles. Such a CCD-camera can be connected to the optical fibre, achieving thereby a very simple structure of the chemical sensor arrangement, avoiding malfunction and especially misalignment between the single components.

Between CCD-camera and the optical fibre, a microscope and/or a UV-filter may be provided.

Instead of the fibre optics and the CCD-camera, it is possible to provide a CCD-chip, whereupon the nanoparticle-indicators are positioned. They may be positioned either on the CCD-chip or on a substrate above the chip. Furthermore, as with the CCD-camera arrangement, a UV-filter may be provided.

The system using the optical fibre and the CCD-camera is especially useful when having to reach locations difficult to access, whereas the arrangement with a CCD-chip is preferred with stationary sensor arrangements.

In one embodiment, the nanoparticles are linked to each other and/or to a substrate, preferably an optical fibre, by bi-functional or poly-functional ligands. These ligands preferably comprise one or more amino groups and/or one or more thiol groups. The ligands may further be chosen from the group comprising mercaptoalkylsilanes, aminoalkylsilanes, dimercapto alkanes, diaminoalkanes and hydroxy- and carboxylalkanes, especially dihydroxyalkanes and dicarboxylalkanes. Not only alkanes, but also other bi- and poly-functional organic or inorganic compounds may be used as ligands.

The ligands interconnecting the nanoparticles are basically of the same length, although it may also be possible to use ligands of a different length. By choosing and/or varying the length of the ligands, the size of the cavities within the nanoparticle assemblies, necessary for the diffusion of the analytes within the structure, can be varied and selected. The chemical sensor may therefore be suited to the desired application and made selective for certain analytes. Also the chemical nature of the linker molecules will influence the chemical selectivity of the nanoparticle assembly.

In a further embodiment the nanoparticles are provided in a defined matrix of a gel, a polymere or a porous inorganic material. The distance between the nanoparticles and the cavities can also be varied and specified, allowing a fitting to certain analytes. Again, the chemical nature of the membrane will influence the selectivity of the nanoparticle assembly.

In a further embodiment, the nanoparticle assemblies are covered by selective membranes. These membranes may act as filters, preventing certain analytes from coming into contact with the nanoparticle indicators. Such a selection may be achieved by pores in the membrane preventing molecules of an analyte exceeding a specific size to penetrate. It is therefore possible to block certain analytes, not wanted to be detected, thereby increasing the sensitivity for other analytes.

In order to gain chemical selectivity, the particles are in one embodiment imbedded into a matrix obtained by molecular imprint technology. The surface of the nanoparticles can also be chemically modified by attaching functional organic molecules, e.g. alkylamines. With such an arrangement, the nanoparticle surface is made selective or specific for certain analytes.

It is a further object of the present invention to achieve a method for providing nanoparticles of defined and of different sizes, especially for a chemical sensor arrangement as described above.

This object is solved by the methods of the present invention.

According to a first method, a nanoparticle solution comprising nanoparticles of a broader size distribution is applied to chromatography beads, whereby nanoparticles are adsorbed on said beads and are classified by size. The chromatography beads are normally provided within a chromatography column.

Therefore, the nanoparticles in the same level of the chromatography column have essentially the same size, whereas there is a gradient of size between the subsequent levels, so that nanoparticles of a specific desired size can be selected.

The beads of specific layer levels, comprising nanoparticles of essentially the same size, are separated from the other layers and are held in a suspension.

Therefore, a number of suspensions, each comprising nanoparticles of essentially the same size, but all suspensions having nanoparticles of different sizes, can be provided. The suspensions with the nanoparticles, adsorbed to the chromatography beads, can then be used for the inventive chemical sensor arrangement as explained above, especially can be applied to a substrate or the optical fibre or to the respective micro-troughs therein.

Preferably, the chromatography beads are silica-beads, $Al_2O_3$ or Sephadex-beads (Sephadex is a registered trademark).

According to a second method, the nanoparticles are classified by means of a thin-layer-chromatography. In this case, the nanoparticles will be distributed over a thin-layer-chromatography plate, having essentially the same size in one level, but showing a size gradient in different levels at the thin-layer-chromatography plate.

The nanoparticles having the desired size can be separated from the thin-layer-chromatography plate, preferably level by level, and can be applied to the above-described chemical sensor arrangement.

It is further possible to take a piece of the thin-layer-chromatography plate together with the classified nanoparticles disposed thereon, whereby the size gradient of the nanoparticles is maintained within this piece. The piece of the plate can then be preferably combined with a sensor arrangement, especially with a CCD-chip of the above described inventive chemical sensor arrangement. Each level can now be considered as a nanoparticle assembly forming the sensor array.

According to a third method, the nanoparticles are classified by means of electrophoresis, preferably by means of gel-electrophoresis. Again, the nanoparticles will be classified depending on the size within the gel. A slice of the gel comprising the classified nanoparticles and therefore comprising a size gradient in one direction, can be taken from the gel. Such a slice can be preferably combined with a CCD-chip of the inventive sensor. Again each level of the slice forms a nanoparticle assembly of the sensor array.

Preferably, the slice has a thickness of less than 1 mm, preferably less than 0.1 mm.

With the above described methods, the sizes of the nanoparticles can be exactly defined and applied to the chemical sensor arrangement of the present invention. The size distribution of the nanoparticles is therefore exactly defined within the sensor arrangement and ensures reliable measurements and analysis.

The size fractionation of nanoparticles can also be performed by size selective precipitation. After size fractionation, samples with different particle sizes are used to build up the sensor array, as described above.

By defining a standard manufacturing procedure, especially according to one of the above described methods, it is further easily possible to manufacture comparable chemical sensor arrangements, showing always the same properties. An adjustment or verification of each sensor arrangement prior to use might therefore be omitted, although of course is always recommended.

Figure 2:
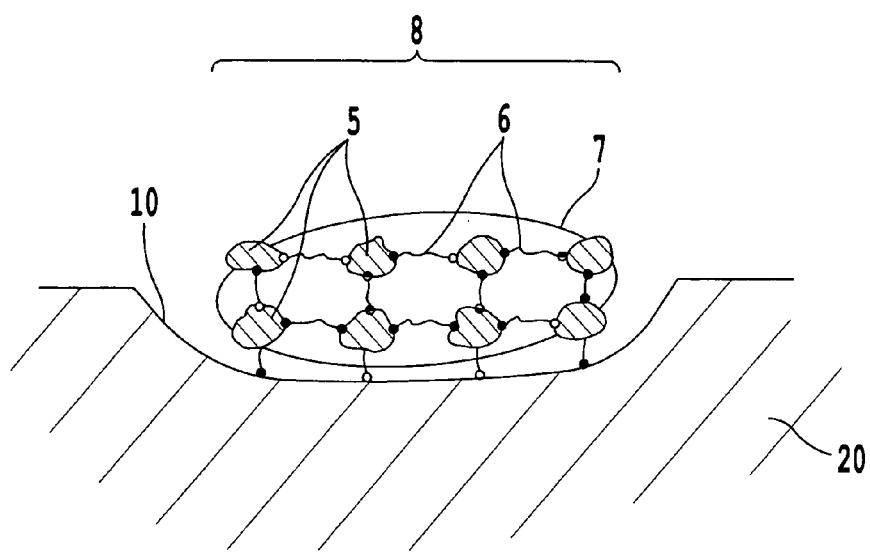
Figure 3:
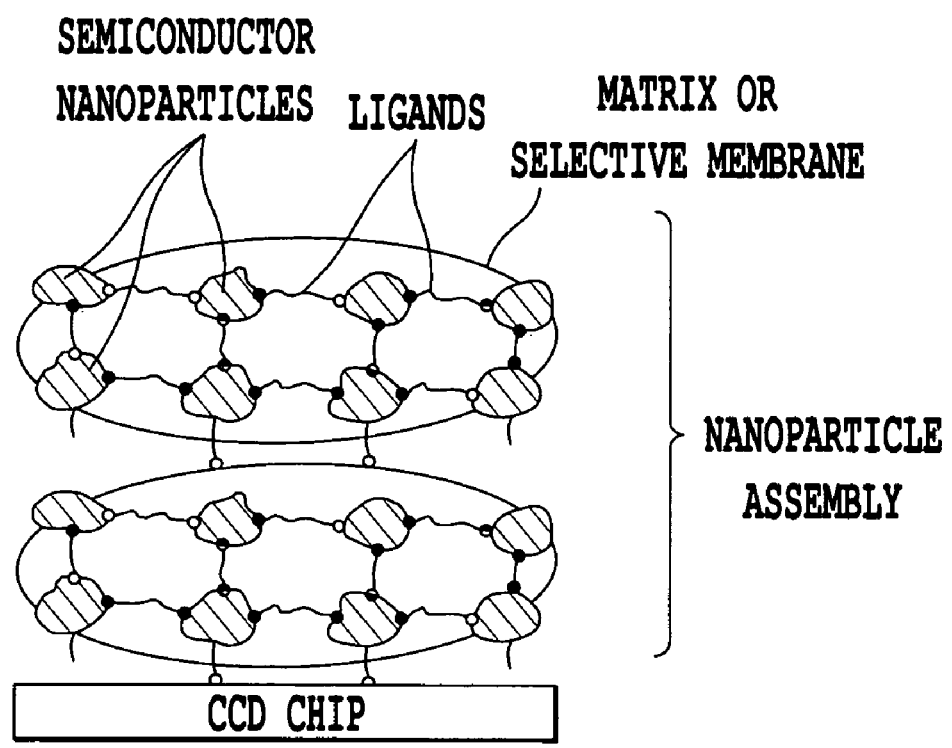

Further features and advantages of the present invention will be apparent from the description of a specific embodiment in connection of the drawings, wherein FIG. 1 schematically shows a measurement system comprising an embodiment of the inventive chemical sensor arrangement, and FIG. 2 schematically shows the nature of the nanoparticle structure within a micro-trough according to an embodiment of the present invention.

In FIG. 1, an embodiment of the inventive chemical sensor arrangement 1 is shown. Semiconductor nanoparticles 5 forming nanoparticle assemblies 8 are provided in micro-troughs 10, formed into the surface of an optical fibre 20. Here an array 9 of nanoparticle assemblies 8 is provided, wherein in different micro-troughs 10 nanoparticle assemblies 8 of different materials are provided.

The nanoparticles 5, forming the assemblies 8, have sizes between 1 and 100 nm and are distributed in micro troughs 10 depending on their size, wherein the micro-troughs have a diameter of approximately 5 μm. Within each micro trough 10 the nanoparticles 5 have essentially the same size and are within a range of ±10% with respect to the desired and/or average size in the respective trough 10.

A current flow and any change in the current flow in the indicator is detected by the means for detecting current flow 70. The change may be the result of analyte absorption.

Any radiation or change of radiation due to a change of the optical properties of the nanoparticle indicators 5, caused by an analyte to be detected, is directly transferred by an optical fibre 20 to a CCD-camera 30. Between fibre optic 20 and CCD-camera 30 a microscope 40 and a UV-filter 50 is provided.

The information detected by the CCD-camera 30 is transferred to a computer or analysis unit 60 and is analysed. Because of the array arrangement of this embodiment, analytes or compositions of analytes to be detected show a specific "reaction pattern", i.e. different optical reactions of each kind of nanoparticles in the respective micro troughs. Thereby a wide range of analytes can be detected with this sensor arrangement.

FIG. 2 schematically shows a cross-sectional view through a micro-trough 10 in the surface of an optical fibre 20.

The micro-trough 10 is filled with a nanoparticle assembly 8 comprising nanoparticles 5, adsorbed to a gel bead 7, wherein the gel bead 7 is only indicated in this figure. The particles 5 are linked to the surface of the micro-trough 10 and linked to one another by polyfunctional ligands 6, comprising amino groups.

The ligands 6, shown here, have all essentially the same lengths, but it is also possible to provide ligands 6 with different lengths in order to tune the nanoparticle indicators 5 to suit to the desired application and the analytes to be expected.

Only for completion, it should be again noticed that the nanoparticles 5 can also be embedded in a matrix (not shown), wherein the distance between the nanoparticles and the pore size can also be selected in order to suit to a specific application and to specific analytes.

The features of the present invention disclosed in the specification, the claims and/or in the accompanying drawings, may, both separately and in any combination thereof, be material for realizing the invention in various forms thereof.

The invention claimed is:

1. A chemical sensor arrangement comprising:
an analyte sensitive indicator;
wherein the analyte sensitive indicator comprises an array of semiconductor nanoparticle assemblies,
wherein each assembly of the array comprises a plurality of nanoparticles,
wherein, within a single assembly, each of the plurality of nanoparticles are of identical semiconductor material,
wherein the plurality of nanoparticles of a first assembly are different from the plurality of nanoparticles of a second assembly, and
wherein within each assembly, the semiconductor nanoparticles have a size between 1 mm and 100 nm, and
wherein optical properties of said nanoparticles change, said change being caused by the analyte to be detected.

2. The chemical sensor arrangement according to claim 1, further comprising:
means for detecting optical properties of the indicator and/or changes thereof; and/or
means for detecting current flow passing through the indicator and changes thereof.

3. The chemical sensor arrangement according to claim 1, wherein nanoparticles showing different sensitivities, selectivities and/or optical properties are provided.

4. The chemical sensor arrangement according to claim 1, wherein a plurality of semiconductor nanoparticles are provided, each of said plurality of nanoparticles having different energy levels.

5. The chemical sensor arrangement according to claim 4, wherein the semiconductor material is selected from a group comprising II/IV semiconductors CdS, CdSe, CdTe, ZnO, ZnS, ZnSe, ZnTe, HgS, HgSe, HgTe, or Cd3 Pa.

6. The chemical sensor arrangement according to claim 4, wherein the semiconductor material is CdS, CdSe, CdTe, ZnO, ZnS, ZnSe, ZnTe, HgS, HgSe, HgTe, or $Cd_3P_2$.

7. The chemical sensor arrangement according to claim 4, wherein the semiconductor material is selected from a group comprising III/V semiconductors.

8. The chemical sensor arrangement according to claim 4, wherein the semiconductor material is GaAs or InP.

9. The chemical sensor arrangement according to claim 4, wherein the identical semiconductor material is a combination of two or more different materials.

10. The chemical sensor arrangement according to claim 4, wherein the identical semiconductor material is a combination of CdSe/ZnS, CdSe/CdS, CdS/Cd(OH)$_2$ or HgS/CdS core/shell structures.

11. The chemical sensor arrangement according to claim 4, wherein the at least one nanoparticle is doped with Lanthanides and/or transition metals.

12. The chemical sensor arrangement according to claim 1, wherein multiple nanoparticles are provided and form a sponge like assembly.

13. The chemical sensor arrangement according to claim 1, wherein the nanoparticles are provided in at least one optical fibre.

14. The chemical sensor arrangement according to claim 1, wherein the nanoparticles are provided in at least one micro-trough.

15. The chemical sensor arrangement according to claim 13, wherein the nanoparticles are provided in at least one micro-trough within at least one optical fibre.

16. The chemical sensor arrangement according to claim 2, wherein the means for detecting optical properties of the indicator comprises a CCD-camera.

17. The chemical sensor arrangement according to claim 2, wherein the means for detecting optical properties of the indicator comprises a CCD-chip and that the at least one nanoparticle is provided on said CCD-chip.

18. The chemical sensor arrangement according to claim 1, wherein multiple nanoparticles forming an assembly are provided, which are at least partially linked to each other and/or to a substrate.

19. The chemical sensor arrangement according to claim 1, wherein multiple nanoparticles forming an assembly are provided, which are at least partially linked to each other and/or to an optical fibre.

20. The chemical sensor arrangement according to claim 1, wherein multiple nanoparticles forming an assembly are provided, which are at least partially linked to each other and/or to a substrate by bi-functional or poly-functional ligands.

21. The chemical sensor arrangement according to the claim 1, wherein the nanoparticles are provided in a defined matrix of a gel, a polymer or a porous inorganic material.

22. The chemical sensor arrangement according to claim 1, wherein the nanoparticles are covered by a selective membrane or are embedded into a matrix, obtained by molecular imprint technology.

23. The chemical sensor arrangement according to claim 22, wherein the membrane or the matrix comprises pores for selecting analytes depending on its molecular size or polarity.

* * * * *

UNITED STATES PATENT AND TRADEMARK OFFICE
CERTIFICATE OF CORRECTION

PATENT NO. : 7,223,367 B1 Page 1 of 1
APPLICATION NO. : 09/533688
DATED : May 29, 2007
INVENTOR(S) : Vossmeyer et al.

It is certified that error appears in the above-identified patent and that said Letters Patent is hereby corrected as shown below:

Column 3, line 8, insert --be-- after "preferably";
        line 44, change "s" to --a--

Column 4, line 22, change "are" to --is--

Column 8, line 11, change "$Cd_3P_a$" to --other semiconductors, as $Cd_3P_2$.--

Signed and Sealed this

Eighth Day of July, 2008

JON W. DUDAS
*Director of the United States Patent and Trademark Office*